United States Patent [19]

McGregor

[11] 3,971,799

[45] July 27, 1976

[54] PREPARATION OF 3,5,6-TRICHLOROPICOLINIC ACID

[75] Inventor: Stanley D. McGregor, Midland, Mich.

[73] Assignee: The Dow Chemical Company, Midland, Mich.

[22] Filed: Dec. 27, 1974

[21] Appl. No.: 537,054

[52] U.S. Cl. .............................................. 260/295 R
[51] Int. Cl.² ...................................... C07D 213/26
[58] Field of Search ............................... 260/295 R

[56] References Cited
UNITED STATES PATENTS 3,317,549   5/1967   Johnston .......................... 260/294.9

OTHER PUBLICATIONS

Chemical Abstracts, 79:18912q, (1973).
Chemical Abstracts, 78:84614z, (1973).
Chemical Abstracts, 75:63559h, (1973).

Primary Examiner—Norman A. Drezin
Attorney, Agent, or Firm—S. Preston Jones

[57] ABSTRACT 3,5,6-Trichloropicolinic acid is prepared in a process which comprises
  a. reacting by contacting tetrachloropicolinic acid, hydrazine and an alkali reaction medium in water;
  b. reacting by contacting the thus formed 3,5,6-trichloro-4-hydrazinopicolinic acid intermediate with an alkali metal hydroxide and an alkaline hypochlorite solution; and
  c. acidifying the reaction mixture with a mineral acid and recovering the desired 3,5,6-trichloropicolinic acid product.

7 Claims, No Drawings

PREPARATION OF 3,5,6-TRICHLOROPICOLINIC ACID

BACKGROUND OF THE INVENTION 3,5,6-Trichloropicolinic acid is a known compound useful as a herbicide and as an agent for the control of pig ascarids. The compound is a white solid melting at 164°–165°C. and is of extremely low solubility in water and petroleum oils and of moderate to high solubility in common organic solvents.

Collins et al., J. Chem. Soc., (c); pages 167–174 (1971) teach that halogens ortho and para to the ring nitrogen in pentachloropyridine are reactive with hydrazine hydrate. This reference further teaches the formation of tetrahalo-4-hydroxy pyridine from the action of aqueous sodium hydroxide on tetrahalo-4-hydrazino pyridines. From this same starting material, 2,3,6-trichloropyridine is formed from the reaction with cuprous oxide in hot water.

SUMMARY OF THE INVENTION

The present invention is directed to a process for the preparation of 3,5,6-trichloropicolinic acid. The process of the present invention comprises:

a. reacting by contacting tetrachloropicolinic acid, hydrazine and an alkali reaction medium in water;

b. reacting by contacting the thus formed 3,5,6-trichloro-4-hydrazinopicolinic acid intermediate with an alkali metal hydroxide and an alkali metal hypochlorite solution; and c. acidifying the reaction mixture with a mineral acid and recovering the desired 3,5,6-trichloropicolinic acid product.

While the process of the present invention can be carried out in separate and distinct steps, with separation of the products of each step, it is within the scope of the present invention to carry out the process in one reaction vessel using sequential reaction steps.

The reactions which occur during the process of the present invention can be exemplified as follows:

In the above exemplification of the reaction steps, M represents an alkali metal from the group hereinafter set forth and X represents an alkaline ion from the group hereinafter set forth. No attempt has been made to present balanced equations.

In carrying out the process of the present invention, the tetrachloropicolinic acid, alkali metal hydroxide or carbonate and hydrazine are added to water with agitation and heated under reflux conditions for a period of from about 15 minutes to about 2 hours or more.

The reaction consumes the reactants in stoichiometric proportions, however, in order to insure completion of the reaction, it is preferred that a slight excess of about 5 to 20 percent of both the alkali metal hydroxide or carbonate and hydrazine be employed.

Representative alkali metal hydroxides or carbonates which can be employed in carrying out this step include sodium, potassium, cesium, lithium and rubidium hydroxides and carbonates.

At the completion of this reaction, the thus formed 3,5,6-trichloro-4-hydrazinopicolinic acid intermediate can be separated, if desired, or the next step of the process can be carried out in situ.

In carrying out this step of the process, the 3,5,6-trichloro-4-hydrazinopicolinic acid is normally first mixed with the aqueous alkali metal hydroxide and the alkaline hypochlorite added thereto. The reaction is normally carried out at room temperature and the reaction is complete in from about 5 minutes to about 1 hour.

At the completion of the above reaction, the reaction is acidified with a mineral acid in order to convert the salt form of the 3,5,6-trichloropicolinic acid to the acid form. After acidification, the product is removed by extraction with a solvent such as, for example, methy-

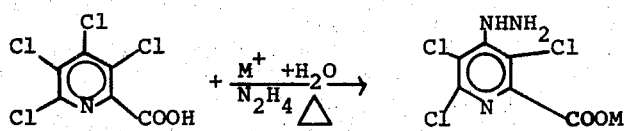

Reaction Step (a)

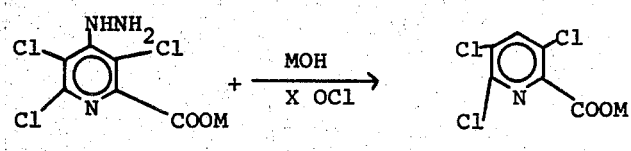

Reaction Step (b)

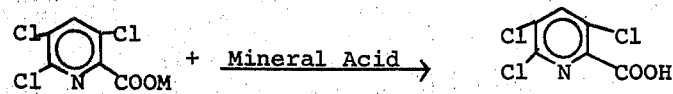

Reaction Step (c)

lene chloride, or by filtration of the precipitated product. The solvent is thereafter removed by evaporation under reduced pressure leaving the product as a crude residue. The product can be purified, if desired, by conventional techniques of sublimation, recrystallization or washing.

Representative alkali metal hydroxides which can be employed in carrying out the process of this invention include the hydroxides of sodium, potassium, cesium, lithium and rubidium.

Representative alkaline hypochlorites which can be employed in the practice of the present invention include the hypochlorites of sodium, potassium, calcium or magnesium.

The amount of the reactants employed is not critical, since some of the product is formed when employing any proportions. While the reaction consumes the reactants in equimolar amounts, completion of the reaction can be assured by employing about a 10–20 percent excess of the alkaline hypochlorite.

DESCRIPTION OF SOME PREFERRED EMBODIMENTS

The following examples illustrate the present invention and the manner by which it can be practiced but, as such, should not be construed as limitations upon the overall scope of the same.

EXAMPLE I

Preparation of 3,5,6-trichloro-4-hydrazino picolinic acid

To a reaction flask containing 200 milliliters of water at the boiling point was added 26.1 grams (0.1 mole) of tetrachloropicolinic acid, 4.1 grams (0.103 mole) of sodium hydroxide in 25 milliliters of water and 3.47 grams (0.105 mole) of hydrazine. The reaction mixture was stirred under reflux for 30 minutes. An additional 4.1 grams (0.103 mole) of sodium hydroxide in 25 milliliters of water was slowly added to the reaction mixture over a 25 minute period and the mixture refluxed for 45 minutes. The reaction mixture was cooled to room temperature and 25 milliliters of 5 Normal hydrochloric acid was added thereto. The solid 3,5,6-trichloro-4-hydrazinopicolinic acid (as the monohydrate) which precipitated was recovered by filtration in a yield of 22.9 grams (83.5 percent of theoretical) and melted at 166°–168°C.

EXAMPLE II

Preparation of 3,5,6-trichloro-4-hydrazino picolinonitrile

To a reaction flask was added 400 milliliters of 95 percent ethanol and 24.2 grams (0.10 mole) of tetrachloropicolinonitrile. The mixture was heated to 45°C. with stirring and 3.7 grams (0.11 mole) of 95 percent hydrazine and 10.1 grams (0.10 mole) of triethylamine was added thereto. The mixture was heated under reflux for 1 hour and the reaction mixture thereafter cooled to 40°C. To this mixture was added 400 grams of an ice-water mixture and the solid 3,5,6-trichloro-4-hydrazinopicolinonitrile product which precipitated was recovered by filtration, water washed and dried. The product was recovered in a yield of 20.6 grams (87 percent of theoretical) melting at 178°–181°C.

EXAMPLE III

Preparation of 3,5,6-trichloro-4-hydrazino picolinic acid

To a reaction vessel containing 50 milliliters of water and 200 milliliters of concentrated sulfuric acid was slowly added, with agitation, 50 grams (0.2 mole) of 3,5,6-trichloro-4-hydrazinopicolinonitrile, prepared as above in Example II. The mixture was heated for 1 hour at 115°–120°C. and the mixture cooled to 50°C. and poured over ice. The solid 3,5,6-trichloro-4-hydrazinopicolinic acid which precipitated was recovered by filtration, water washed and successively washed with methanol, benzene, and hexane. The product (as the sulfate salt) was obtained in a yield of 54 grams (88 percent of theoretical) melting at 206°–207°C.

EXAMPLE IV

Preparation of 3,5,6-trichloropicolinic acid

A mixture was prepared by admixing 3 grams (0.01 mole) of 3,5,6-trichloro-4-hydrazinopicolinic acid with 15 milliliters of 20 percent sodium hydroxide and 20 milliliters of water. To this mixture at 30°C was added 25 milliliters (0.018 mole) of a 5.25 percent sodium hypochlorite solution. Immediate gas evolution was noted which ceased after about 3 minutes. Five minutes after the addition of the sodium hypochlorite solution, the reaction mixture was acidified to a pH of about 2 with concentrated hydrochloric acid. The mixture was extracted with methylene chloride. The methylene chloride was removed from the extract by evaporation leaving 2.5 grams of the crude 3,5,6-trichloropicolinic acid which was purified by sublimation at 130°C and 1 millimeter of mercury. There was thus obtained 2.0 grams of the purified product (88 percent of theoretical) which melted at 147°–151°C.

What is claimed is:

1. A process of preparing 3,5,6-trichloropicolinic acid which comprises:
   a. reacting, by contacting under reflux conditions for from about 15 minutes to about 2 hours, stoichiometric proportions of tetrachloropicolinic acid and hydrazine in the presence of an excess of an alkali metal reaction medium in water;
   b. reacting, by contacting for about 5 minutes to about 1 hour, the thus formed 3,5,6-trichloro-4-hydrazinopicolinic acid intermediate with from about a 10 to 20 percent excess of an alkaline hypochlorite in the presence of an aqueous alkali metal hydroxide; and
   c. acidifying the reaction mixture to a pH of about 2 with a mineral acid and recovering the 3,5,6-trichloropicolinic acid product.

2. The process as defined in claim 1 wherein the alkali reaction medium is sodium hydroxide.

3. The process as defined in claim 1 wherein the alkali metal hydroxide is sodium hydroxide.

4. The process as defined in claim 1 wherein the alkaline hypochlorite is sodium hypochlorite.

5. The process of claim 2 wherein the alkali metal hydroxide is sodium hydroxide and the alkaline hypochlorite is sodium hypochlorite.

6. A process for preparing 3,5,6-trichloropicolinic acid which comprises:
   a. reacting, by contacting for about 5 minutes to about 1 hour, 3,5,6-trichloro-4-hydrazinopicolinic acid with a 10 to 20 percent stoichiometric excess of an alkaline hypochlorite and an aqueous alkali metal hydroxide, and
   b. acidifying the reaction mixture to a pH of about 2 with a mineral acid and recovering the 3,5,6-trichloropicolinic acid product.

7. The process as defined in claim 6 wherein the alkali hydroxide is sodium hydroxide and the alkaline hypochlorite is sodium hypochlorite.

* * * * *